United States Patent [19]

Stiefel

[11] Patent Number: 4,620,015

[45] Date of Patent: Oct. 28, 1986

[54] SYNTHESIS OF β-((2-METHYLPROPOXY)METHYL)-N-PHENYL-N-(PHENYLMETHYL)-1-PYRROLIDINEETHANAMINE

[75] Inventor: Frank J. Stiefel, Princeton Junction, N.J.

[73] Assignee: Carter-Wallace, Inc., New York, N.Y.

[21] Appl. No.: 521,895

[22] Filed: Aug. 10, 1983

Related U.S. Application Data

[63] Continuation-in-part of Ser. No. 334,535, Dec. 28, 1981, abandoned.

[51] Int. Cl.$^4$ .......................................... C07D 207/08
[52] U.S. Cl. ..................................... 548/547; 564/367
[58] Field of Search ........................................ 548/547

[56] References Cited

U.S. PATENT DOCUMENTS 2,568,778  9/1951  Surrey et al. .................. 546/169 X 3,962,238  6/1976  Mauvernay et al. ................ 546/547

Primary Examiner—Glennon H. Hollrah
Assistant Examiner—D. B. Springer
Attorney, Agent, or Firm—Kevin B. Clarke

[57] ABSTRACT

A novel, efficient, economical procedure for the synthesis of ethers of n-propanoldiamine having the formula:

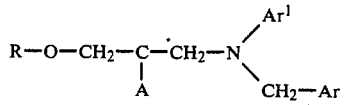

wherein R is a straight or branched chain lower alkyl group or an aralkyl group, Ar is an aromatic group, Ar$^1$ is an aromatic or heterocyclic group, A is a tertiary aliphatic, cycloaliphatic or heterocyclic amino group and addition salts thereof with pharmacologically acceptable acids.

2 Claims, No Drawings

SYNTHESIS OF β-((2-METHYLPROPOXY)METHYL)-N-PHENYL-N-(PHENYLMETHYL)-1-PYRROLIDINEETHANAMINE

This application is a continuation-in-part of pending U.S. patent application Ser. No. 06/334,535 filed Dec. 28, 1981, now abandoned.

This invention relates to the preparation of ethers of n-propanoldiamine having the general formula:

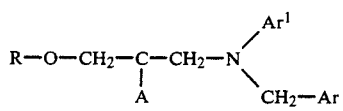

in which A is a tertiary aliphatic, cycloaliphatic or heterocyclic amino group, R is a straight or branched chain lower alkyl group or an aralkyl group, Ar is an aromatic group and $Ar^1$ is an aromatic or heterocyclic group, and addition salts thereof with pharmacologically acceptable acids.

When Ar and $Ar^1$ are both aromatic groups, they may be the same or different. Ar and $Ar^1$ may both be monocyclic aromatic groups and $Ar^1$ may be a heteromonocyclic group which may contain a nuclear nitrogen atom with or without an additional nuclear hetero atom.

The ethers prepared in accordance with the present invention have found utility in the treatment of various cardiovascular conditions.

Earlier U.S. Patents, i.e. U.S. Pat. No. 3,962,238 and U.S. Pat. No. Re. 30,577, disclose the preparation of ethers of n-propanoldiamine such as B-[(2-methylpropxy)methyl]-N-phenyl-N-(phenylmethyl)-1-pyrrolidineethanamine commonly called bepridil, wherein amino alcohols having the general formula:

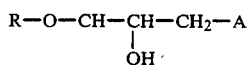

in which R is a straight or branched chain lower alkyl group or an aralkyl group and A is a tertiary aliphatic, cycloaliphatic or heterocyclic amino group, are reacted with thionyl chloride dissolved in a suitable solvent such as chloroform in order to obtain the corresponding chloro compounds having the general formula:

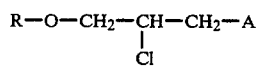

in which R and A are as defined above.

The compounds thus obtained are then condensed with amines having the general formula:

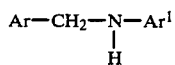

wherein Ar is an aromatic group and $Ar^1$ is an aromatic or heterocyclic group, which have previously been converted to their sodium derivatives by reaction with sodium amide, to obtain the ethers of n-propanoldiamine.

The multi-step synthesis described in the prior art referred to above produces an overall yield of approximately 20%. I have now found a more efficient and economical process for the manufacture of ethers of n-propanoldiamine which produces an overall yield of approximately 50%.

Essentially the present invention eliminates several steps of the prior art process thereby avoiding the handling and isolation of intermediates as well as a distillation step. In addition, the condensing step is carried out utilizing sodium hydride dispersed in mineral oil, a much safer and more reactive condensing agent. Further, the use of sodium hydride as a condensing agent in lieu of sodium amide of the prior art eliminates the occurence of a significant number of reaction by-products, i.e. ammonia.

Moreover, I have unexpectedly found that by a careful choice of a petroleum solvent during the sodium hydride condensation reaction, the rapid addition of ingredients to the reaction will not result in an uncontrolled exothermic reaction. Normally, toluene has been used as the solvent of choice during the sodium hydride condensation reaction. The rapid addition of ingredients to the condensation reaction can lead to an uncontrolled exothermic reaction. Surprisingly I have found that this phenomenon can be eliminated when xylene is employed as the solvent.

Moreover, unlike the viscous liquid obtained by prior processes, the final product of the present process is isolated as a solid, thereby doing away with the difficult and expensive distillation steps of the prior art.

In accordance with the present invention ethers of n-propanoldiamine are prepared by first reacting at elevated temperatures lower alkyl alcohols, i.e. alcohols containing from 3 to 6 carbon atoms, with epichlorohydrin in the presence of a Lewis Acid. The reaction mixture is cooled and reacted with pyrrolidine and the reaction mixture rendered alkaline by the addition of a base such as sodium hydroxide. Upon completion of the reaction, the mixture is extracted with a petroleum solvent such as toluene, xylene, etc. and combined with thionyl chloride and the mixture heated to reflux. The heated mixture is then decomposed by the addition of water, rendered alkaline by addition of a base such as sodium hydroxide, and the oil layer and petroleum solvent extract of the aqueous layer are recovered and concentrated. The concentrate is condensed with a condensing agent such as sodium amide or preferably sodium hydride dispersed in mineral oil in the presence of N-benzylaniline and a petroleum solvent such as toluene or preferably xylene. The reaction mixture is cooled and the desired n-propanoldiamine ether as the solid hydrochloride is recovered.

As an example of the preferred embodiment of the present invention following is the synthesis of bepridil:

275 g. of isobutanol (3.676 moles) is placed in one liter three neck round bottom flask equipped with a stirrer and condenser. 225 g. of epichlorohydrin (2.45 moles) and 5 g. of powdered anyhdrous zinc chloride are added with stirring. The reaction mixture is heated on a steam bath at 95° C. for approximately twenty-four hours. The mixture is cooled at 40° C. and 213 g. of pyrrolidien (3.0 moles) is added. Cooling is continued to approximately 15° C. and 196 g. (2.45 moles) of a 50% sodium hydroxide solution diluted with 250 ml. of water is dripped into the mixture. After all the alkali has been added, remove the cooling bath and continue stirring. The temperature slowly rises to 70°–80° C. Stirring is continued for one-half hour and then the mixture is heated to 95° C. on a steam bath for half an hour. 250 ml. of water is added and the mixture let cool to room temperature. The mixture is extracted with 300 ml. of toluene and the extract is washed with 250 ml. of water. The extract is concentrated and distilled to obtain 364 g. of product B.P. 146°-9° C. @ 25 mm. $n^{27}d=1.4565$ having the following structure:

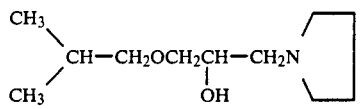

Compound I 166 g. (1.39 moles) of thionyl chloride are dissolved in 110 ml. of toluene in a 1 liter three neck round bottom flask equipped with a dropping funnel, thermometer, stirrer and condenser. A solution of 166 gm. of Compound I dissolved in 110 ml. of toluene is dripped in. The temperature rises to 90° C. during the addition and the thionyl chloride refluxes. Reflux is continued for two hours after addition is completed and then the solution is concentrated in vacuo on a steam bath. The concentrate is decomposed by the careful addition of 200 ml. of water and made alkaline with 200 g. of 50% NaOH in 400 ml. of water. The oily layer is separated and the aqueous layer is extracted with 200 ml. of toluene. The oil layer and extract are combined and washed with 200 ml. of water. The product is concentrated in vacuo on a steam bath and may be used directly. However, distillation of the chloroamine can be done but with much foaming. The boiling point of the product is 136°-139° C. @ 17 mm. $n^{20}d=1.4606$ and the yield is 85%. The structure of the compound is:

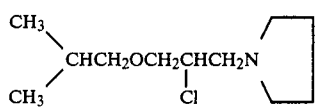

Compound II 15 g. of 50% sodium hydride dispersed in mineral oil (0.21 moles) is placed in a 500 ml. round bottom flask equipped with a dropping funnel, stirrer and condenser whose exit port is connected to a bubbler containing xylene. 150 ml. of xylene is added to the sodium hydride, stirred and heated to 130° C. A solution of 50 g. of Compound II (0.23 moles) and 33 g. of N-benzylaniline (0.21 moles), dissolved in 150 ml. of xylene is dripped in and the temperature is maintained at 130°-135° C. A steady stream of hydrogen bubbles will appear. The addition is adjusted to product an even flow of hydrogen. After all the material is added heating at 130°-135° C. with stirring is contined for two hours. The reaction mixture is cooled to 25° C. and decomposed slowly with 40 ml. of methanol and then 200 ml. of water. The xylene layer is concentrated in vacuo and 150 ml. of 10% hydrochloric acid is added and stirring contined for 10 minutes. The reaction is diluted with 400 ml. of water, cooled to room temperature, and seeded. The product is filtered and washed with water and a small amount of cold xylene to remove oil. Air dry overnight and then in vacuo at 60° C. 70 g. of Compound III M.P. 88°-90° C. having the following structure is obtained:

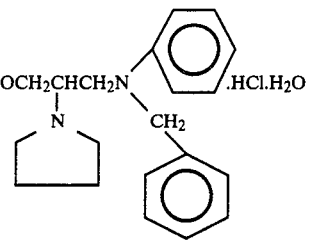

Compound III

The foregoing Compound III is useful in the form of its addition salts with pharmaceutically acceptable organic and inorganic salts such as hydrochloric acid and fumaric acid, which can be prepared by conventional and well known methods.

While the preferred embodiment of the present invention has been described in connection with the preparation of bepridil it will be readily apparent to those skilled in the art that the method described is applicable to a series of n-propanoldiamine ethers by substituting the appropriate intermediates containing the required reactive sites.

What is claimed is:

1. A process for preparing the n-propanoldiamine ether, β-[(2-methypropoxy)methyl]-N-phenyl-N-(phenylmethyl)-1-pyrrolidineethanamine and its hydrochloride salts consisting essentially of the following steps:
   (a) reacting isobutanol with epichlorohydrin at elevated temperature in the presence of a Lewis acid;
   (b) cooling the reaction mixture of step (a) and combining the mixture with pyrrolidine and dilute sodium hydroxide, extracting the mixture with a petroleum solvent, and distilling the product;
   (c) combining the product of step (b) with thionyl chloride dissolved in a petroleum solvent and heating the mixture to reflux;
   (d) decomposing the reaction mixture of step (c) with water, rendering the decomposed mixture alkaline, separating the oily layer from the acqueous layer, extracting the acqueous layer with petroleum solvent, combining and washing the oily layer and extract and distilling at elevated temperatures and reduced pressure;
   (e) condensing the concentrate of step (d) with n-benzylaniline utilizing sodium hydride dispersed in a solution of xylene and mineral oil as a condensing agent and recovering the desired N-propaneoldiamine ether as its hydrochloride salt.

2. A process according to claim 1 wherein said Lewis Acid is anhydrous zinc chloride.

* * * * *